US00PP25628P3

(12) United States Plant Patent
Radler

(10) Patent No.: US PP25,628 P3
(45) Date of Patent: Jun. 23, 2015

(54) SHRUB ROSE PLANT NAMED 'RADGOR'

(50) Latin Name: *Rosa hybrida*
Varietal Denomination: Radgor

(71) Applicant: CP Delaware, Inc., Wilmington, DE (US)

(72) Inventor: William J. Radler, Greenfield, WI (US)

(73) Assignee: CP Delaware, Inc., Wilmington, DE (US)

( * ) Notice: Subject to any disclaimer, the term of this patent is extended or adjusted under 35 U.S.C. 154(b) by 111 days.

(21) Appl. No.: 13/987,449

(22) Filed: Jul. 26, 2013

(65) Prior Publication Data

US 2015/0033421 P1 Jan. 29, 2015

(51) Int. Cl.
*A01H 5/02* (2006.01)

(52) U.S. Cl.
USPC ..... Plt./107

(58) Field of Classification Search
USPC ..... Plt./107, 106
CPC ..... A01H 5/0216; A01H 5/0222
See application file for complete search history.

*Primary Examiner* — Kent L Bell

(74) *Attorney, Agent, or Firm* — Buchanan, Ingersoll & Rooney PC

(57) ABSTRACT

A new and distinct shrub rose plant is provided that abundantly forms attractive semi-double shell pink blossoms having yellow centers. The plant exhibits vigorous vegetation and a mounding and bushy growth habit. The foliage is dark green with a semi-glossy finish on the upper surface. The light blossom coloration contrasts nicely with the dark green foliage. The disease resistance is excellent, particularly with respect to black spot. The plant is well suited for providing attractive ornamentation in the landscape.

2 Drawing Sheets

Botanical/commercial classification: *Rosa hybrida*/Shrub Rose Plant.

Varietal denomination: cv. Radgor.

SUMMARY OF THE INVENTION

The new variety of *Rosa hybrida* landscape shrub rose plant of the present invention was created during 2004 at Greenfield, Wis., U.S.A. The seed that produced the new variety of landscape shrub rose was from mixed parents of unreleased and unnamed breeding plants (each non-patented in the United States). No further definitive information concerning the identity of the parents is available.

The seeds resulting from the above pollination were sown and small plants were obtained which were physically and biologically different from each other. Selective study resulted in the identification of a single plant of the new variety.

It was found that the new Landscape Shrub rose plant of the present invention possesses the following combination of characteristics:

(a) abundantly forms attractive semi-double shell pink blossoms having yellow centers,
(b) exhibits a mounding and bushy growth habit,
(c) forms vigorous vegetation,
(d) forms attractive dark green foliage with a semi-glossy finish on the upper surface that contrasts well with the blossom coloration,
(e) exhibits excellent disease resistance particularly with respect to black spot, and
(f) is well suited for growing as attractive ornamentation in the landscape.

A new rose variety is provided having semi-double shell pink blossoms with yellow centers combined with substantially continuous blooming and excellent black spot resistance.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention also can be readily distinguished from other shrub rose plants including the 'Sprothrive' variety (U.S. Plant Pat. No. 23,549) through an inspection of the blossoms. For instance, the shell pink blossoms of the new variety are dissimilar to the dark red blossoms of the 'Sprothrive' variety.

The characteristics of the new variety have been found at Wasco, Calif., U.S.A., to be homogeneous and stable and to be strictly transmissible by asexual propagation, such as budding, grafting, and the rooting of cuttings from one generation to another. The new variety reproduces in a true-to-type manner by such asexual propagation.

The new variety has been named 'Radgor', and will be marketed under the THRIVE! SEASHELL trademark.

BRIEF DESCRIPTION OF THE PHOTOGRAPHS

The accompanying photographs show, as nearly true as it is reasonably possible to make the same in color illustrations of this character, typical flowering rose plants of the new variety. The illustrated rose plants of the new variety were approximately two years of age and were observed during May while growing outdoors on their own roots at West Grove, Pa., U.S.A.

DETAILED BOTANICAL DESCRIPTION

Figure 1:
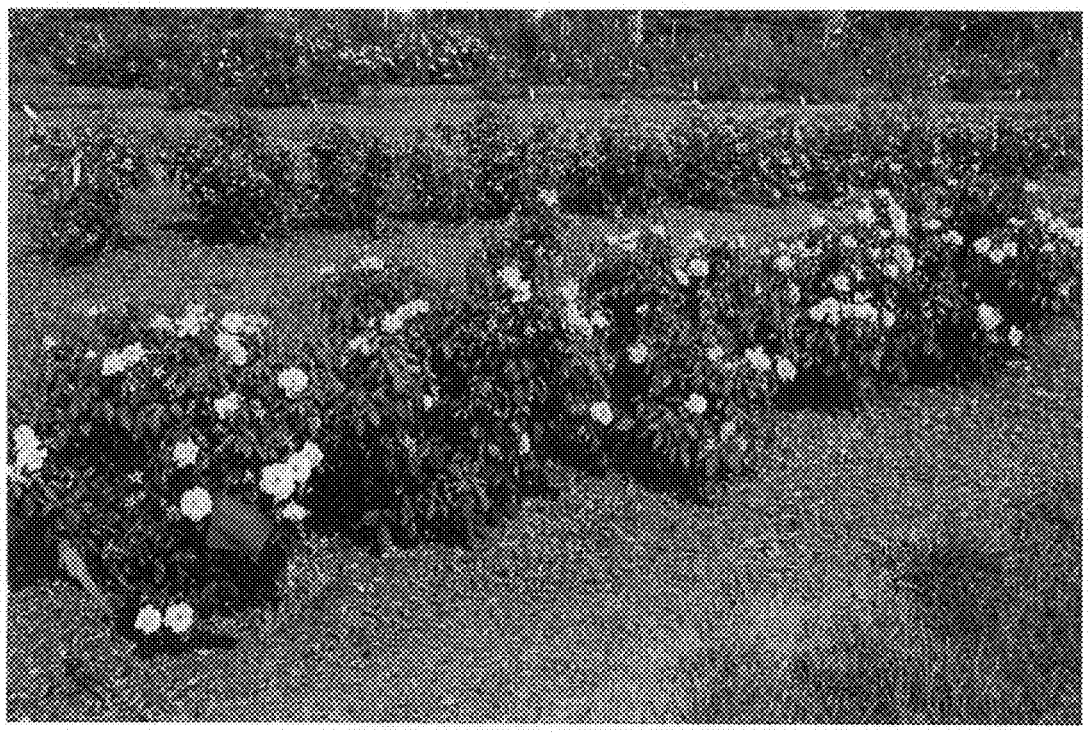
FIG. 1 shows in the forefront a row of blossoming shrub rose plants of the new variety wherein the typical growth habit and dark green foliage are illustrated.
Figure 2:
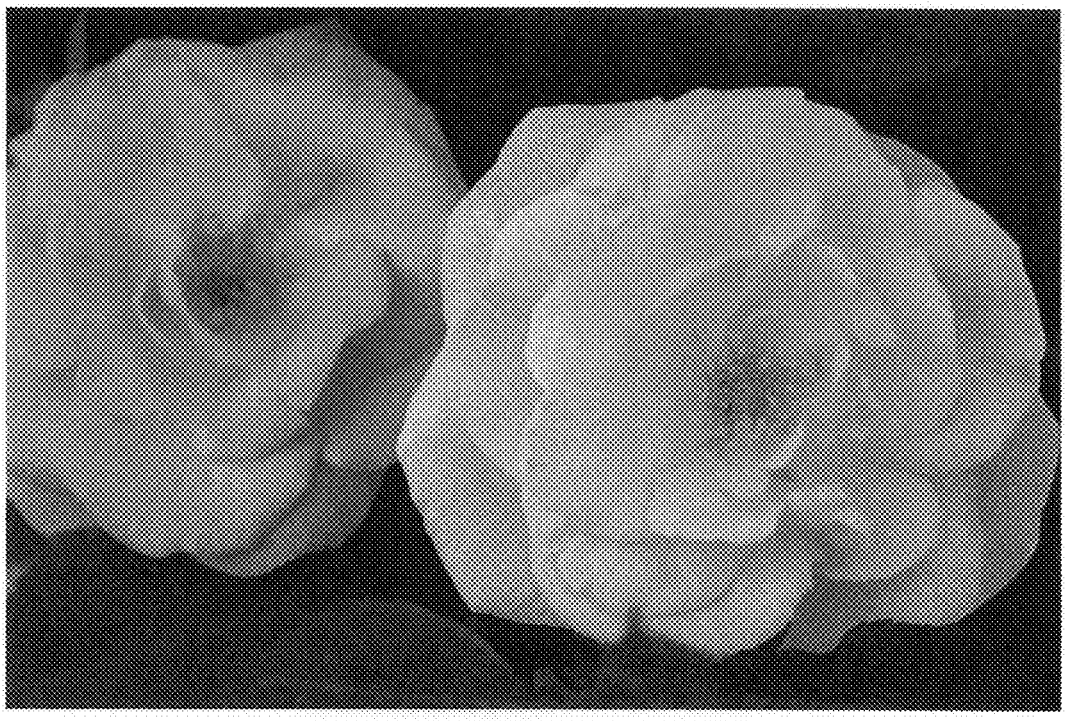
FIG. 2 shows an obverse view of a pair of fully open semi-double blossoms of the new variety wherein the shell pink overall coloration with yellow coloration at the center is illustrated.

The chart used in the identification of colors is that of The Royal Horticultural Society (R.H.S. Colour Chart—1995 Edition or equivalent), London, England. The description is based on the observation of two-year-old specimens of the new variety during July while growing in containers outdoors on their own roots at West Grove, Pa., U.S.A.

Class: Landscape Shrub Rose. Cultivar 'Radgor'.

Plant:

*Height*.—Approximately 60 cm on average and commonly approximately 90 cm on average at full maturity.

*Width*.—Approximately 60 cm on average and commonly approximately 90 to 120 cm on average at full maturity.

*Habit*.—Mounding and bushy.

Branches:

*Color*.—Near Yellow-Green Group 144A on young stems, and commonly near Grey-Brown Group 199A on mature wood.

*Diameter*.—Up to approximately 3 cm for the main stem and up to approximately 1 cm for secondary stems.

*Thorns*.—Size: commonly approximately 1 cm in length on average when mature. Color: commonly near Greyed-Orange Group 177A on young stems, and near Greyed-Green Group 197A when mature.

Leaves:

*Size*.—Commonly approximately 11 cm in length on average and approximately 8 cm in width on average for a five-leaflet leaf.

*Leaflets*.—Number: 3, 5, and 7. Length: approximately 5.5 cm on average for a terminal leaflet, and approximately 3 cm on average for a lower leaflet. Width: approximately 3 cm on average for a terminal leaflet, and approximately 2 cm on average for a lower leaflet. Shape: ovate. Base: obtuse. Margins: serrate. Texture: generally smooth on the upper and under surfaces. Overall appearance: attractive dark green leaves with a semi-glossy upper surface. Color: (when young): Upper surface: near Green Group 138A. Under surface: near Yellow-Green Group 147B. Color (when fully mature): Upper surface: near Green Group 139A. Under surface: near Green Group 137B.

Inflorescence:

*Number of flowers*.—Commonly one per stem or up to approximately 5 blooms in a cluster, and approximately 20 blooms on the plant at a given time.

*Peduncle*.—Near Green Group 138A in coloration, commonly approximately 3 cm in length on average, approximately 3 mm in diameter on average, smooth in texture, and commonly covered with small flexible thorns less than 1 mm in length.

*Sepals*.—Shape: generally lanceolate. Apex: acuminate. Margin: entire and commonly with extensions on three of the five extensions that measure approximately 1 cm in length at most. Upper surface: covered with short hairs, and commonly near Green Group 139C in coloration. Under surface: covered with short hairs, and commonly near Yellow-Green Group 144A in coloration. Size: commonly approximately 2.3 cm in length on average, and approximately 8 mm in width at the base. Number: five.

*Buds*.—Shape: generally ovoid. Length: approximately 1.5 cm on average as the calyx breaks. Diameter: approximately 1 cm on average as the calyx breaks. Color: near Red Group 52B towards the apex blending to near Yellow-Orange Group 21B at the base.

*Flower*.—Form: semi-double, cuplike. Diameter: commonly approximately 6.5 cm on average when opening and approximately 8 cm on average when fully open. Depth: commonly approximately 2.5 cm on average when opening and approximately 2 cm on average when fully open. Color (when opening): Upper surface: near Yellow-Orange Group 14C at the point of attachment, transitioning to Red-Purple Group 65C, and finally Red-Purple Group 65A towards the apex. Under surface: near Yellow Group 10C at the point of attachment blending to Red-Purple Group 65A towards the apex. Color (at end of blooming): Upper surface: near Yellow-White Group 158C at the point of attachment, transitioning to Red Group 56C, and finally Red Group 56A towards the apex. Under surface: Orange-White Group 159D at the point of attachment blending to Red Group 55C towards the apex. Fragrance: none noticeable. Petal number: commonly approximately 10 to 15 on average under normal growing conditions. Petal length: commonly approximately 3.4 cm on average. Petal width: commonly approximately 3.6 cm on average. Petal shape: obcordate. Petal margin: entire, slightly recurved. Petal apex: broadly obcordate. Petal base: broadly cuneate. Petal drop: good, the petals commonly detach cleanly and freely drop upon full maturity. Stamen number approximately 100 on average. Anthers: commonly near Greyed-Orange Group 163A in coloration. Filaments: approximately 7 mm in length, and the coloration is near Yellow-Orange Group 17B towards the tip and near Yellow Group 8B at the base. Pollen: commonly present in a moderate quantity and near Greyed-Orange Group 163A in coloration. Pistils: separate and free, and commonly number approximately 57 on average. Styles: commonly approximately 3 mm in length, commonly less than 1 mm in diameter, and near Red-Purple Group 59D in coloration. Stigma: commonly less than 1 mm in length, commonly less than approximately 0.5 mm in diameter, and near Green-White Group 157A in coloration. Receptacle: commonly spherical in shape, approximately 6 mm in diameter, smooth in texture, near Yellow-Green Group 144D in coloration, and with achenes commonly being present on the bottom and wall. Hips/seeds: none observed.

Development:

*Vegetation*.—Vigorous and strong.

*Blossoming*.—Abundant and substantially continuous from spring to first frost.

*Resistance to diseases*.—Excellent, particularly with respect to black spot.

Plants of the 'Radgor' variety have not been observed under all possible environmental conditions to date. Accordingly, it is possible that the phenotypic expression may vary somewhat with changes in light intensity and duration, cultural practices, and other environmental conditions.

I claim:

1. A new and distinct Landscape Shrub rose plant characterized by the following combination of characteristics:

(a) abundantly forms attractive semi-double shell pink blossoms having yellow centers, (b) exhibits a mounding and bushy growth habit, (c) forms vigorous vegetation, (d) forms attractive dark green foliage with a semi-glossy finish on the upper surface that contrasts well with the blossom coloration, (e) exhibits excellent disease resistance particularly with respect to black spot, and (f) is well suited for growing as attractive ornamentation in the landscape; substantially as herein illustrated and described.

* * * * *